US011242467B2

(12) United States Patent
Boerzsoenyi et al.

(10) Patent No.: US 11,242,467 B2
(45) Date of Patent: Feb. 8, 2022

(54) MELAMINE-POLYETHERS AS DISPERSANTS IN NON-AQUEOUS, LIQUID PIGMENT COMPOSITIONS

(71) Applicant: BASF SE, Ludwigshafen am Rhein (DE)

(72) Inventors: Gabor Boerzsoenyi, Ludwigshafen (DE); Tibor Duris, Ludwigshafen (DE); Stephan Weinkoetz, Ludwigshafen (DE); Frank Reuter, Ludwigshafen (DE); Frank Pirrung, Ludwigshafen (DE)

(73) Assignee: BASF SE

( * ) Notice: Subject to any disclaimer, the term of this patent is extended or adjusted under 35 U.S.C. 154(b) by 581 days.

(21) Appl. No.: 16/071,120

(22) PCT Filed: Jan. 20, 2017

(86) PCT No.: PCT/EP2017/051134
§ 371 (c)(1),
(2) Date: Jul. 19, 2018

(87) PCT Pub. No.: WO2017/125524
PCT Pub. Date: Jul. 27, 2017

(65) Prior Publication Data
US 2020/0332142 A1    Oct. 22, 2020

(30) Foreign Application Priority Data

Jan. 22, 2016    (EP) ..................................... 16152449

(51) Int. Cl.
| C09D 17/00 | (2006.01) |
| C09D 7/65 | (2018.01) |
| C09D 7/45 | (2018.01) |
| C07D 251/54 | (2006.01) |
| C07D 403/06 | (2006.01) |
| C08G 73/02 | (2006.01) |
| C09D 133/00 | (2006.01) |

(52) U.S. Cl.
CPC ......... *C09D 17/002* (2013.01); *C07D 251/54* (2013.01); *C07D 403/06* (2013.01); *C08G 73/0273* (2013.01); *C09D 7/45* (2018.01); *C09D 7/65* (2018.01); *C09D 133/00* (2013.01)

(58) Field of Classification Search
None
See application file for complete search history.

(56) References Cited

U.S. PATENT DOCUMENTS

| 3,920,645 A | 11/1975 | Schibler et al. |
| 4,013,655 A | 3/1977 | Merz et al. |
| 4,822,372 A | 4/1989 | Forster et al. |
| 5,157,075 A * | 10/1992 | Kanai ................... A61K 8/492 524/17 |
| 5,760,226 A | 6/1998 | Niessner et al. |

FOREIGN PATENT DOCUMENTS

| DE | 23 65 752 A1 | 6/1976 |
| JP | 49-005901 A | 1/1974 |
| JP | 49-015797 A | 2/1974 |
| JP | 63-089599 A | 4/1988 |
| JP | 10-502965 A | 3/1998 |
| JP | 2009-235167 A | 10/2009 |
| KR | 10-2010-0001668 A | 1/2010 |

OTHER PUBLICATIONS

Li et al. (Advanced Materials Research vols. 450-451 pp. 374-378 (Year: 2012).*
Frank Pirrung, et al., "Chapter 4, Polymeric Dispersants," Macromolecular Engineering, Precise Synthesis, Materials Properties, Applications (ed. K. Matyjaszewski et al.), Apr. 9, 2007, pp. 2135-2180.
Li Yanshan, et al., "Preparation and characterization of melamine/formaldehyde/polyethylene glycol crosslinking copolymers as solid-solid phase change materials," Solar Energy Materials & Solar Cells, vol. 127, Apr. 14, 2014, pp. 92-97.
S.M. Levi, et al., "Tanning properties of compounds containing methylol groups", Tr. Vses. Nauchn.-Issled. Kinofotoinst (1962), No. 51, 80-94, XP002755182, Database Chemical Abstract Service 1964, 3 pages (Abstract only).
Zygmunt Wirpsza, et al., "Melamine presspowder modified with bis-urethanes and bis-ethers of glycols with monohydroxymethylmelamine," Prepr. Short. Contrib.—Bratislava IUPAC Int. Conf. Modif. Polym. 5th (1979), vol. 1, 49, XP002755181, Database Chemical Abstracts Service 1968, 9 pages.
International Search Report dated Feb. 22, 2017 in PCT/EP2017/051134 filed Jan. 20, 2017.
Elmstahl et al., "Materials Science Monographs", Compos. Syst. Nat. Synth. Polym., 36, 1986, pp. 75-82.

* cited by examiner

*Primary Examiner* — Robert T Butcher
(74) *Attorney, Agent, or Firm* — Faegre Drinker Biddle & Reath LLP

(57) ABSTRACT

The present invention relates to novel mono- or polynuclear melamine compounds and their use as dispersants for pigments and fillers in coating compositions, in particular in solvent-borne coating compositions. The mono- or polynuclear melamine compounds of the invention have at least one 2,4,6-triamino-1,3,5-triazine ring, wherein at least one amino groups of at least one of the 2,4,6-triamino-1,3,5-triazine rings of the mono- or polynuclear melamine compounds is of the formula A:NR$^1$R$^2$ (A) where R$^1$ is H, CH(R$^3$)OR$^4$ or R$^2$, R$^2$ is CH(R$^3$)O(A-O)$_x$—R$^5$, where R$^3$ is H, C$_1$-C$_{10}$-alkyl or aryl; R$^4$ is H, C$_1$-C$_4$-alkyl or C$_1$-C$_4$-alkoxy-C$_1$-C$_4$-alkyl; R$^5$ is a hydrocarbon radical having from 1 to 40 carbon atoms; x is an integer from 2 to 500, having on average a value in the range from 2.5 to 400; A is an C$_2$-C$_4$-alkan-1,2-diyl radical.

20 Claims, No Drawings

MELAMINE-POLYETHERS AS DISPERSANTS IN NON-AQUEOUS, LIQUID PIGMENT COMPOSITIONS

The present invention relates to novel mono- or polynuclear melamine compounds and their use as dispersants for pigments and fillers in coating compositions, in particular in solvent-borne coating compositions.

BACKGROUND OF THE INVENTION

Pigments are ordinarily organic or inorganic dry powders that incorporate a mixture of primary particles, aggregates and agglomerates. For both industrial and consumer coating compositions, whether solvent borne or water borne, the pigment should be dispersed homogeneously throughout the coating composition in order to ensure a uniform appearance of the final coating. To be properly dispersed, pigments are usually wetted, deaggregated and deagglomerated in a vehicle to obtain a dispersion of the pigment particles. Wetting involves incorporation of the pigment into the vehicle replacing pigment-air interfaces with pigment-vehicle interfaces. Wetting agents facilitate bringing pigments into a dispersed state as a result of surface activity at the pigment-solution interface. An ideal pigment dispersion consists of a homogenous suspension of particles, after reducing the size of any aggregates and agglomerates.

While some organic vehicles may be good pigment wetting agents themselves, dispersants are typically added to the liquid vehicle to ensure thorough pigment dispersion throughout the vehicle. Dispersants can also be used to temporarily stabilize the pigment dispersion from re-aggregating and re-agglomerating. Problems that occur with current available pigment compositions include (i) a separation or settling of the compositions into their components over time which can require periodic remixing or stirring, and (ii) an undesirable change in rheological profile.

Liquid pigment compositions containing pigments and fillers and a liquid vehicle are used in an almost unlimited number of different technical applications, in particular for colouring coating compositions, including solvent and water-borne paints, heavy duty coatings, automotive coatings, in printing inks, or for colouring cosmetics, plastics etc.

The function of dispersants is manifold. Mainly, they act as stabilizers for the solid fine particulate materials in the liquid pigment compositions, i.e. the dispersant separates the particles of the solid fine particulate material and thus prevents them from coagulation or clumping and settling from the liquid vehicle. They also may act as solubilizers in the given carrier liquid of a coating composition. Dispersants may also improve the optical properties of the coatings, such as gloss, colour intensity or rub-out characteristics. Depending on the type and polarity of the vehicle, e.g. water, organic solvents or mixtures thereof, polymers of variable structure are used as dispersants.

A general survey on the different types of polymeric dispersants, their polymeric architecture and their properties is given by F. Pirrung and C. Auschra in Macromolecular Engineering, Precise Synthesis, Materials Properties, Applications (ed. K. Matyjaszewski et al.), chapter 4, polymeric dispersants, pp. 2135-2180.

Although a large number of dispersants for pigment compositions have been described in the art, there is still a need for dispersants, which provide for a good rheological behavior of the pigment composition and which allow for formulation of pigment compositions, which can be easily incorporated in solvent borne coating compositions, which provide a high color strength and also for good rub out characteristics. For economical reasons, dispersants are required, which can be produced in a simple manner using readily available starting materials. Moreover, the dispersants should be compatible with other ingredients of the pigment compositions and the coating compositions.

L. Yanshan et al., Solar Energy Materials & Solar Cells, 127 (2014), 92-97 describe solid-solid phase change materials based on highly crosslinked melamine polymers, which are obtained by the reaction of melamine, formaldehyde and polyethylene glycol.

S. M. Levi et al., "Tanning properties of compounds containing methylol groups", Tr. Vses. Nauchn.-Issled. Kinofotoinst. Vol. 51, 1962, 80-94 describe the mononuclear melamine compound N2,N2,N4,N4,N6,N6-hexakis[[2-(2-methoxyethoxy)ethoxy]-methyl]-1,3,6-triazine-2,3,6-triamine.

Wirpsza et al., Prepr. Short. Contrib.—Bratislava IUPAC Int. Conf. Modif. Polym. $5^{th}$ (1979), Vo. 1, 49 describe the condensation of binuclear melamine compounds of the formula A with formaldehyde. The compounds are suggested for use in melamine presspowder.

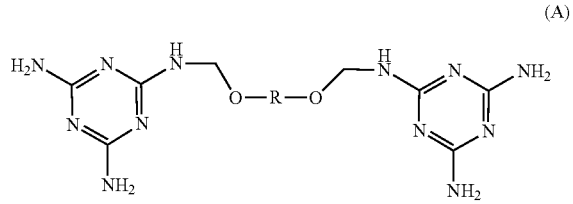

(A)

R=$(CH_2)_4$ or $(CH_2CH_2O)_n CH_2CH_2$, where n is 1, 6, 8 or 21.

SUMMARY OF THE INVENTION

It was surprisingly found that the above problems are solved by the mono- and polynuclear melamine compounds described hereinafter and mixtures thereof. These mono- or polynuclear melamine compounds as well as their mixtures are suitable as dispersants for fine particulate materials, such as pigments and fillers in organic vehicles and therefore allow the preparation of liquid pigment compositions, which can be easily incorporated into solvent borne coating compositions.

Therefore, a first aspect of the present invention relates to the mono- and polynuclear melamine compounds and mixtures thereof, as described hereinafter.

The mono- or polynuclear melamine compounds of the invention have at least one 2,4,6-triamino-1,3,5-triazine ring, wherein at least one amino groups of at least one of the 2,4,6-triamino-1,3,5-triazine rings of the mono- or polynuclear melamine compounds is of the formula A:

$NR^1R^2$  (A)

where
$R^1$ is H, $CH(R^3)OR^4$ or $R^2$,
$R^2$ is $CH(R^3)O(A-O)_x$—$R^5$, where
  $R^3$ is H, $C_1$-$C_{10}$-alkyl or aryl;
  $R^4$ is H, $C_1$-$C_4$-alkyl or $C_1$-$C_4$-alkoxy-$C_1$-$C_4$-alkyl;
  $R^5$ is a hydrocarbon radical having from 1 to 40 carbon atoms;
  x is an integer from 2 to 500, having on average a value in the range from 2.5 to 400;
  A is an $C_2$-$C_4$-alkan-1,2-diyl radical.

The new mono- or polynuclear melamine compounds of the invention and their mixtures can be prepared by the following to processes 1 and 2, as described herein. These processes are also part of the invention.

Process 1 is a two step process and comprises the following steps:
 a) reacting 2,4,6-triamino-1,3,5-triazine and an aldehyde of the formula $R^3$—CHO and optionally an alcohol $R^{4a}$—OH,
 b) reacting the reaction product of step a) with a polyether of formula (II)

$$R^5\text{—}[O\text{-}A]_x OH \quad (II)$$

and optionally with an alcohol $R^8$—OH,
wherein $R^3$, $R^5$, $R^8$ A and x are as defined herein and $R^{4a}$ has one of the meanings given for $R^4$ but is different from hydrogen.

Process 2 is a single-step process and comprises reacting a polyether of formula (II), as defined above, with 2,4,6-triamino-1,3,5-triazine and an aldehyde of the formula $R^3$—CHO, wherein $R^3$ is as defined herein, and optionally an alcohol $R^{4a}$—OH or $R^8$—OH.

Both process 1 and process 2 are polycondensation reactions, which result in a mixture of mono- and polynuclear melamine compounds, which can either be separated or used as mixtures.

The mono- or polynuclear melamine compounds of the invention and also their mixtures, in particular the mixtures, which are obtained by the processes of the invention, are suitable as dispersants for pigment materials and work in particular in hydrophobic carriers. They provide for a good rheological behavior of the pigment composition and allow for formulation of pigment compositions, which can be easily incorporated in solvent borne coating compositions, which provide a high color strength and also for good rub out characteristics.

Therefore, the present invention also relates to the use of the melamine compounds as described herein, as well as of their mixtures, as dispersants in non-aqueous, i.e. solvent based, liquid pigment compositions, in particular in pigment pastes and colorants.

The present invention also relates to non-aqueous, i.e. solvent-based, liquid pigment composition, comprising a melamine compound as described herein, a pigment component and a non-aqueous diluent.

DETAILED DESCRIPTION OF THE INVENTION

Here and in the following, the term "pigment component" relates to pigments and mixtures of at least one pigment and at least one particulate non-pigment material, hence, filler.

The term "mono- or polynuclear melamine compound" is understood to mean a compound which has at least one radical derived from 2,4,6-triamino-s-triazine, wherein at least one of the amino groups of at least one of the melamine radicals contained in the mono- or polynuclear melamine compounds is a radical of the formula (A) as described herein. A mononuclear melamine compound has a single radical derived from 2,4,6-triamino-s-triazine, while a polynuclear melamine compound has at least 2, e.g. from 2 to 20, radicals derived from 2,4,6-triamino-s-triazine, depending on the molecular weight of the polynuclear melamine compound. A polynuclear melamine compound which has 2 radicals derived from 2,4,6-triamino-s-triazine will also be termed as binuclear melamine compound, while a polynuclear melamine compound which has 3 radicals derived from 2,4,6-triamino-s-triazine will also be termed as trinuclear melamine compound, and so on.

It is apparent to a skilled person that a mononuclear melamine compound of the invention has 3 amino groups, where at least one of these amino groups is of the formula (A) as described herein. It is also apparent to a skilled person that a binuclear melamine compound of the invention has 6 amino groups, where at least one of these amino groups is of the formula (A) as described herein and where 2 amino groups are linked by a bivalent linker as described herein. It is also apparent to a skilled person that a polynuclear melamine compound of the invention, which has m radicals derived from 2,4,6-triamino-s-triazine, will have 3m amino groups, where at least one of these amino groups is of the formula (A) as described herein and where 2(m−1) amino groups are linked in pairs by a bivalent linker as described herein.

It is apparent to a skilled person that in the mono- or polynuclear melamine compound of the invention, those amino groups, which are not of the formula (A) and which are not linked by a linker may be primary amino groups, i.e. $NH_2$, secondary amino groups $NHR^x$ and tertiary amino groups $NR^xR^y$, where $R^x$ and $R^y$ are organic radicals different from hydrogen and e.g. radicals $CH(R^3)OR^4$ or $CH(R^3)O\text{—}R^8$, where $R^3$, $R^4$ and $R^8$ are as defined herein.

For example, a mono-nuclear melamine compound will have the following formula M1

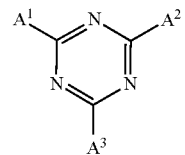

where at least one of the radicals $A^1$, $A^2$ and $A^3$ is a radical of the formula (A), while the remaining radicals are of the formulae $NHR^x$ or $NR^xR^y$, respectively.

For example, a binuclear melamine compound can be described by the following formula M2

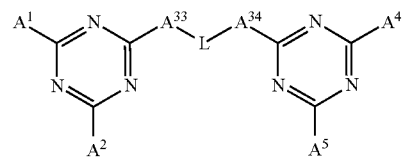

where at least one of the radicals $A^1$, $A^2$, $A^4$ and $A^5$ is a radical of the formula (A), while the remaining radicals $A^1$, $A^2$, $A^4$ and/or $A^5$ are of the formulae $NHR^x$ or $NR^xR^y$, respectively. L is a bivalent linker, e.g. linear or branched alkandiyl, which is optionally interrupted by oxygen atoms, such as $CH(R^3)$ or a $CH(R^3)[O\text{—}CH(R^3)]_k$, where k is an integer, which is frequently in the range from 1 to 5, and where $R^3$ is as defined herein. $A^{33}$ and $A^{34}$ are typically radicals $NR^z$, where $R^z$ is hydrogen or an organic radical different from hydrogen, such as a radical $CH(R^3)OR^4$ or $CH(R^3)O\text{—}R^8$, where $R^3$, $R^4$ and $R^8$ are as defined herein.

It is apparent that a polynuclear melamine compound, which is different from a binuclear melamine compound, can be described by the following formula M3,

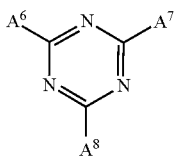

where at least one of the radicals $A^6$, $A^7$ and $A^8$ is a radical of the formula Ma

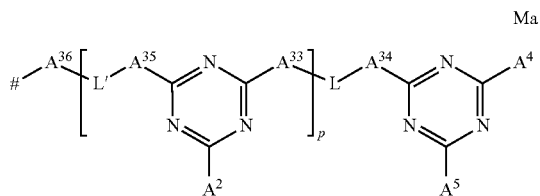

wherein p is 0 or an integer, e.g. from 1 to 20, provided that in at least one of the groups Ma the variable p is different from 0, # indicates the point of attachment to the triazine ring of M3,

L and L' are identical or different bivalent linkers as defined for L in formula M2, $A^{33}$, $A^{34}$, $A^{35}$ and $A^{36}$ are typically radicals $NR^z$, where $R^z$ is as defined for formula M2, provided at least one of the radicals $A^2$, $A^4$, $A^5$, $A^6$, $A^7$ and $A^8$ is a radical of the formula (A), while the remaining radicals $A^2$, $A^4$ and $A^5$, are of the formulae $NHR^x$ or $NR^xR^y$, respectively, and the remaining radicals $A^6$ and $A^7$, are of the formulae Ma, $NHR^x$ or $NR^xR^y$, respectively.

Hydrocarbon radicals having 1 to 40 carbon atoms include but are not limited to:
i. alkyl having 1 to 40 carbon atoms,
ii. alkenyl having 2 to 40 carbon atoms,
iii. cycloalkyl having 3 to 10 carbon atoms, which may be substituted by 1 to 6 alkyl groups, each of which may have 1 to 6 carbon atoms,
iv. aryl having 6 to 10 carbon atoms, which may be substituted by 1 to 6 alkyl groups, each of which may have 1 to 6 carbon atoms,
v. alkyl having 1 to 6 carbon atoms, which is substituted by cycloalkyl having 6 to 10 carbon atoms, which cycloalkyl may be substituted by 1 to 6 alkyl groups, each of which may have 1 to 6 carbon atoms,
vi. alkyl having 1 to 6 carbon atoms, which is substituted by aryl having 6 to 10 carbon atoms, which may be substituted by 1 to 6 alkyl groups, each of which may have 1 to 6 carbon atoms.

Here and in the following the prefix $C_n$-$C_m$ indicates the number of carbon atoms a radical or compound may have. For example, the prefix $C_1$-$C_4$ indicates that the radical, moiety or compound may have from 1 to 4 carbon atoms.

Alkyl denominates a saturated linear or branched, acyclic hydrocarbon radical, which may have from 1 to 40 carbon atoms ($C_1$-$C_{40}$-alkyl). The term $C_1$-$C_4$-alkyl indicates alkyl having from 1 to 4 carbon atoms, such as methyl, ethyl, n-propyl, 2-propyl, n-butyl, 2-butyl, isobutyl, 1,1-dimethylethyl. The term $C_1$-$C_6$-alkyl indicates alkyl having from 1 to 6 carbon atoms, such as methyl, ethyl, n-propyl, 2-propyl, n-butyl, 2-butyl, isobutyl, 1,1-dimethylethyl, n-pentyl, 2-pentyl, neopentyl, n-hexyl, 2-hexyl, 2-methylpentyl, 1,3-dimethylbutyl, 1-ethylbutyl, 2-ethylbutyl, etc. The term $C_1$-$C_{10}$-alkyl indicates alkyl having from 1 to 10 carbon atoms, such as $C_1$-$C_6$-alkyl mentioned before and also, n-heptyl, 1-methylhexyl, 2-methylhexyl, 3-methylhexyl, 4-methylhexyl, 5-methylhexyl, 1-ethylpentyl, 2-ethylpentyl, 3-ethyl pentyl, n-octyl, 1-methylheptyl, 2-methylheptyl, 1-ethylhexyl, 2-ethylhexyl, 1,2-dimethylhexyl, 1-propylpentyl, 2-propylpentyl, n-nonyl, decyl, 2-propylheptyl, and 3-propylheptyl. The term $C_6$-$C_{20}$-alkyl indicates alkyl having from 6 to 20 carbon atoms, such as n-hexyl and its isomers, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methylheptyl, 2-methylheptyl, 1-ethylhexyl, 2-ethylhexyl, 1,2-dimethylhexyl, 1-propylpentyl, 2-propylpentyl, n-nonyl, decyl, 2-propylheptyl, 3-propylheptyl, n-undecyl, n-dodecyl, n-tridecyl, n-tetradecyl, n-hexadecyl, n-octadecyl, n-eicosyl, n-docosenyl (behenyl), lignoceryl and constitutional isomers of the aforementioned n-alkyl radicals.

Alkenyl denominates an ethylenically unsaturated linear or branched hydrocarbon radical, which may have from 2 to 40 carbon atoms ($C_2$-$C_{30}$-alkenyl) and which may have 1, 2, 3 or 4 C=C double bonds.

Cycloalkyl denominates a saturated mono- or bicyclic hydrocarbon radical having usually 3 to 10 carbon atoms, monocyclic radicals such as cyclopropyl, cyclobutyl, cyclopentyl, cycloheptyl, cyclooctyl, etc. Examples of bicyclic radicals comprise bicyclo[2.1.1]hexyl, bicyclo[2.2.1]heptyl, bicyclo[3.1.1]heptyl, bicyclo[2.2.1]heptyl, bicyclo[2.2.2]octyl and bicyclo[3.2.1]octyl.

Aryl denominates an aromatic hydrocarbon atom such as phenyl or naphthyl, which may have a fused carbocyclic ring, such as in indanyl, indenyl, fluoranyl etc. Aryl denominates in particular phenyl and naphthyl.

Alkylen and Alkandiyl denominate linear or branched, saturated bivalent hydrocarbon radicals having usually 1 to 8 carbon atoms, such as methylene, 1,2-ethandiyl, 1,1-ethandiyl, 1,1-propandiyl, 1,2-propandiyl, 2,2-propandiyl, 1,3-propandiyl, 2-methyl-2,3-propandiyl, 1,1-butandiyl, 1,2-butandiyl, 2,2-butandiyl, 2,3-butandiyl, 1,3-butandiyl and 1,4-butandiyl. Likewise, alkantriyl and alkantetrayl, denominate linear or branched, saturated tri- and tetravalent hydrocarbon radicals having usually 1 to 8 carbon atoms, such as ethan-1,1,2-triyl, propan-1,2,3-triyl.

The term $C_2$-$C_4$-alkan-1,2-diyldenominates a bivalent hydrocarbon radical having from 2 to 4 carbon atoms. Examples of $C_2$-$C_4$-alkan-1,2-diyl include ethan-1,2-diyl, propan-1,2-diyl, butan-1,2-diyl, and 2-methylpropan-1,2-diyl.

Alkendiyl denominates linear or branched, unsaturated bivalent hydrocarbon radicals having usually 2 to 8 carbon atoms, such as ethen-1,1-diyl (C=$CH_2$), ethen-1,2-diyl, (—CH=CH—), propen-1,2-diyl (—CH=C($CH_3$)—), propen-2,3-diyl (—$CH_2$—C(=$CH_2$)—) or propen-1,3-diyl (—$CH_2$—CH=CH—). Likewise, alkantriyl and alkantetrayl, denominate linear or branched, saturated tri- and tetravalent hydrocarbon radicals having usually 2 to 8 carbon atoms, such as propen-1,2,3-triyl (—CH=CH(—)—$CH_2$—).

Cycloalkandiyl denominates cyclic saturated bivalent hydrocarbon radicals having usually 3 to 8 carbon atoms, such as cyclopropane-1,1-diyl, cyclopropane-1,2-diyl, cyclobutan-1,1-diyl, cyclobutan-1,2-diyl, cyclobutan-1,3-diyl, cyclopentan-1,1-diyl, cyclopentan-1,2-diyl, cyclopentan-1,3-diyl, cyclohexan-1,1-diyl, cyclohexan-1,2-diyl, cyclohexan-1,3-diyl or cyclohexan-1,4-diyl.

A skilled person will readily understand that the variable x relates to the number of repeating units O-A in the polyether group $O(A-O)_x$—$R^5$ and that number of repeating units in the molecules contained in a sample is not identical for each molecule contained in the sample but represents an average. Therefore, the number average is frequently in the range from 2.5 to 400, in particular from 3 to 100, more particularly 4 to 80 and especially 5 to 60 or 5 to 30.

It is also apparent for a skilled person that the radical $O(A-O)_x$—$R^5$ in formula (A) stems from the polyether of formula (II), while the radical $R^3$ stems from the aldehyde $R^3$—CHO. It is also apparent that any radical $OR^4$ and $OR^8$ stems from alcohols used in processes 1 and 2.

The variables A, x and $R^5$ in the group $CH(R^3)O(A-O)_x$—$R^5$, and likewise in the polyether of the formula (II) may individually on their own and preferably in combination have the following meanings:
  A is selected from the group consisting of ethan-1,2-diyl and propan-1,2-diyl and combinations thereof;
  x is an integer having a number average value in the range from 3 to 200, in particular 3 to 100, more particularly 4 to 80 and especially 5 to 60 or 5 to 30;
  $R^5$ is $C_1$-$C_{22}$-alkyl, aryl-$C_1$-$C_4$-alkyl or aryl, where aryl in the last two mentioned radicals is unsubstituted or carries 1 or 2 $C_1$-$C_{10}$-alkyl groups, where the aforementioned $C_1$-$C_{10}$-alkyl groups, if present, are in particular $C_1$-$C_4$-alkyl groups and especially methyl groups.

More particularly, the variables A, x and $R^5$ in the group $CH(R^3)O(A-O)_x$—$R^5$, and likewise in the polyether of the formula (II) may individually on their own and preferably in combination have the following meanings:
  A is ethan-1,2-diyl;
  x is an integer having a number average value in the range from 5 to 60, especially in the range from 5 to 30;
  $R^5$ is $C_1$-$C_4$-alkyl, especially methyl.

Apart from that, the radical $R^1$ in formula (A) is preferably hydrogen.

In addition to the group of formula (A), one ore more of the melamine rings in the mono- or polynuclear melamine compounds may bear a group of formula (B):

$$NR^6R^7 \qquad (B)$$

where
  $R^6$ is H or $CH(R^3)OR^4$,
  $R^7$ is $CH(R^3)O$—$R^8$, where
    $R^3$ is H, $C_1$-$C_{10}$-alkyl or aryl;
    $R^4$ is H, $C_1$-$C_4$-alkyl or $C_1$-$C_4$-alkoxy-$C_1$-$C_4$-alkyl;
    $R^8$ is a hydrocarbon radical having from 1 to 40 carbon atoms;

In the context of formulae (A) and (B), the radical $R^3$ in the radicals $CH(R^3)OR^4$, $CH(R^3)OR^8$ and $CH(R^3)O(A-O)_x$—$R^5$, respectively, is preferably different from hydrogen and in particular selected from $C_1$-$C_4$-alkyl and phenyl, more particularly $C_1$-$C_4$-alkyl and especially ethyl.

In the context of formulae (A) and (B), the radical $R^4$ in the radical $CH(R^3)OR^4$ is preferably different from hydrogen and is in particular $C_1$-$C_4$-alkyl.

In the context of formula (B), the radical $R^6$ is preferably hydrogen.

In the context of formula (B), the radical $R^8$ is preferably $C_8$-$C_{20}$-alkyl or $C_8$-$C_{20}$-alkenyl.

According to the invention at least one of the amino groups of at least one of the melamine radical contained in the mono- or polynuclear melamine compound is a radical of the formula (A) as described herein.

In particular, at least 10 mol-%, in particular at least 15 mol-% and especially at least 20 mol-% or at least 25 mol-% of the total number of amino groups bound to an s-triazine ring in the compounds of the invention are an amino group of formula (A). An amino group of formula (A) result from the reaction of an amino group of the s-triazine with the aldehyde $R^3$—CHO and the polyether of formula (II) and optionally an alcohol $R^{4a}$—OH. The amount of amino groups of formula (A) may be as high as 100 mol-% in mono-nuclear melamine compounds and up to 95 mol-% in polynuclear melamine compounds, in each case based on the total number of amino groups bound to the s-triazine rings of the mono- or polynuclear melamine compounds. Frequently, it does not exceed 90 mol-% of the total number of amino groups bound to an s-triazine ring in the compounds of the invention.

Frequently, at least 30 mol-%, in particular at least 45 mol-%, especially at least 60 mol-% or at least 75 mol-% of the melamine rings, i.e. the s-triazine rings, bear at least one amino group of formula (A).

The amount of amino groups of the formula (B), will generally not exceed 50 mol-% or 30 mol-%, of the total number of amino groups bound to an s-triazine ring in the compounds of the invention. If present, the amount of amino groups of the formula (B), will generally be in the range from 1 to 50 mol-% in particular from 5 to 30 mol-%, of the total number of amino groups bound to an s-triazine ring in the compounds of the invention. In another embodiment of the invention, the mono- or polynuclear melamine compounds of the present invention do not contain no or virtually no amino groups of formula (B).

Besides the amino groups of formulae (A) and (B), the mono- or polynuclear melamine compounds may contain one or more amino groups of formula (C)

$$NR^9R^{10} \qquad (C)$$

where
  $R^9$ is H or $CH(R^3)OR^4$,
  $R^{10}$ is $CH(R^3)O$—$R^4$, where
    $R^3$ is H, $C_1$-$C_{10}$-alkyl or aryl, and
    $R^4$ is H, $C_1$-$C_4$-alkyl or $C_1$-$C_4$-alkoxy-$C_1$-$C_4$-alkyl,
and/or amino groups (D), which are linked to an amino group of another triazine ring via a bivalent linker, such as $CH(R^3)$ or a $CH(R^3)[O$—$CH(R^3)]_k$, where k is an integer, which is frequently in the range from 1 to 5, and where $R^3$ is as defined herein. Together with amino groups of formulae (A) and (B), the amino groups (C) and (D) will frequently amount to at least 90 mol-%, in particular at least 95 mol-% or at least 99 mol-% of the total number of amino groups bound to an s-triazine ring in the compounds of the invention. Amino groups (D), which are linked to an amino group of another triazine ring via a bivalent linker, can be described by the formula $NR^z$, where $R^z$ is hydrogen or an organic radical different from hydrogen, such as a radical $CH(R^3)OR^4$ or $CH(R^3)O$—$R^8$, where $R^3$, $R^4$ and $R^8$ are as defined herein.

A skilled person will readily understand that the mol-% ages given here are average numbers based on the molecules present in a sample of the mono or polynuclear melamine compound.

With regard to the capability of the mono- or polynuclear melamine compounds of the present invention to act as dispersants, the amount of the radicals $O(A-O)_x$—$R^5$ is frequently at least 10% by weight and up to 99% by weight, based on the total weight of the melamine compound. Frequently, the amount of the radicals $O(A-O)_x$—$R^5$ is in the range from 20 to 95% by weight, in particular from 30 to 90% by weight, based on the total weight of the melamine compound.

Due to the presence of the radicals $O(A-O)_x$—$R^5$ and also due to the potential presence of more than one s-triazine ring, the melamine compounds have to be considered as oligomers of polymers, respectively. The number average weight of these compounds is frequently in the range from 320 to 200000, in particular from 520 to 120000, especially from 600 to 12000. The number average molecular weight can be determined by gelpermeation chromatography (GPC).

As outlined above, the mono- and polynuclear melamine compounds of the invention can be prepared by both process 1 and process 2. Both processes will result in comparable products, which frequently will contain a mixture of mono- and polynuclear melamine compounds as described herein. However, processes 1 and 2 can be conducted in a manner to specifically yield a mononuclear melamine compound.

In step a) of process 1 of the invention it is preferred to react 2,4,6-triamino-1,3,5-triazine, an aldehyde of the formula $R^3$—CHO and an alcohol $R^{4a}$—OH, which is preferably a primary $C_1$-$C_4$-alkanol, such as methanol, ethanol, n-propanol, n-butanol or iso-butanol or a secondary alcohol such as isopropanol or 2-butanol. Preferred aldehydes are those, wherein $R^3$ is different from hydrogen. Preferred aldehydes include $C_2$-$C_4$-alkanals such as acetaldehyde, propionaldehyde or butyraldehyde, and benzaldehyde or substituted benzaldehyde, with particular preference given to $C_2$-$C_4$-alkanals, especially to propanal.

The reaction of the aldehyde of the formula $R^3$—CHO with the amino groups in 2,4,6-triamino-1,3,5-triazine results in a semi-aminal group, i.e. a group of formulae NH—CH($R^3$)OH or N—(CH($R^3$)OH)$_2$ or Schiff's base N=C($R^3$) or. Both, the semiaminal and Schiff's base may undergo a reaction with the alcohol $R^{4a}$—OH, thus forming a moiety NH—CH($R^3$)—OR$^{4a}$ or N(CH($R^3$)—OR$^{4a}$)$_2$ either by etherification of the hydroxyl group of the semi-aminal or by addition of the alcohol $R^{4a}$—OH to the C=N-bond.

The relative amount of aldehyde $R^3$—CHO used in step a) is frequently in the range from 0.25 to 3.0 mol, in particular from 0.3 to 2.5 mol, especially from 0.35 to 2.3 mol per mol of NH$_2$-groups in the 2,4,6-triamino-1,3,5-triazine or from 0.75 to 9 mol, in particular from 0.9 to 7.5 mol, especially from 1.05 to 6.9 mol per mol of 2,4,6-triamino-1,3,5-triazine. If present, the amount of alcohol $R^{4a}$—OH is usually at least 0.2, in particular at least 0.5 mol, especially at least 1 mol per mol of aldehyde $R^3$—CHO. The alcohol $R^{4a}$—OH may also be used as a solvent and thus, its amount may be e.g. as high as to 100 mol or up to 50 mol per mol of the aldehyde.

Step a) of process 1 can be performed by analogy to the methods for producing melamine formaldehyde precondensates as described in Kirk-Othmer, Encyclopedia of Chemical Technology, 3rd edition, Vol. 2, pp. 440-469, U.S. Pat. No. 4,918,317, EP 26914, EP 218887, EP 319337, EP 383,337, EP 415273, DE 19833347, DE 19835114 and WO 01/51197.

Frequently, the reaction is performed by mixing the aldehyde $R^3$—CHO and melamine in the desired amount, optionally in a solvent, such as water or an alcohol $R^{4a}$—OH. The reaction is normally achieved by simply by mixing the reactants of step a) and optionally warming the mixture of the aldehyde $R^3$—CHO and melamine and optionally the solvent, such as water or an alcohol $R^{4a}$—OH, to the reaction temperature. The reaction temperature is frequently in the range from 30 to 80° C., in particular form 35 to 70° C. The reaction of step a) is usually performed at ambient pressure, but it can also be performed at reduced pressure or slightly increased pressure. Normally, the reaction of step a) will be performed at a pressure in the range from 900 to 1200 hPa. Preferably step a) is performed in the absence of an acidic or basic catalyst.

In step b) the intermediate of step a) is reacted with the polyether of formula (II).

The amount of polyether of formula (II) used in the reaction of step b) will frequently be at least 10 mol-%, in particular at least 15 mol-% and especially at least 20 mol-% or at least 25 mol-% based on the total number of amino groups present in the reaction product of step a). The amount of polyether of formula (II) may be as high as 200 mol-% in particular up to 180 mol-%, based on the total number of amino groups present in the reaction product of step a). Frequently, it is in the range from 30 to 120 mol-%, based on the total number of amino groups present in the reaction product of step a).

Frequently, the amount of polyether of formula (II) used in the reaction of step b) will be at least 30 mol-%, in particular at least 45 mol-%, especially at least 60 mol-% or at least 75 mol-% of the melamine rings present in the reaction product of step a).

Frequently, the amount of polyether of formula (II) used in the reaction of step b) will be in the range from 10 to 99% by weight, based on the total weight of the intermediate formed in step a). Preferably, the amount of polyether of formula (II) used in the reaction of step b) will be in the range from 20 to 95% by weight, in particular from 30 to 90% by weight, based on the total weight of the intermediate formed in step a).

A part of the polyether of formula (II) may be replaced by an alcohol of the formula $R^8$—OH, where $R^8$ is as defined above. However, the amount of the alcohol of the formula $R^8$—OH will generally not exceed 50 mol-%, in particular 30 mol-%, based on the total amount of alcohol $R^8$—OH and polyether of formula (II). If present, the amount of the alcohol of the formula $R^8$—OH will frequently in the range from 1 to 50 mol-% in particular from 5 to 30 mol-%, based on the total amount of alcohol $R^8$—OH and polyether of formula (II). Preferably, no alcohol of formula $R^8$—OH is present in the reaction of step b) of process 1.

The reaction of step b) is frequently performed in the presence of an acidic or a basic catalyst, preferably an acidic catalyst and in particular a Broenstedt acid catalyst. However, Lewis acid catalysts can also be used. The amount of catalyst is frequently in the range from 0.05 to 2% by weight, in particular from 0.1 to 1% by weight, based on the total weight of the reactants, i.e. the intermediate formed in step a), the polyether of formula (II) and optionally the alcohol $R^8$—OH, if present. Suitable Broenstedt catalysts include but are not limited to organic sulfonic acids, e.g. alkylsulfonic acids, such as methyl or ethylsulfonic acid and arylsulfonic acid such as phenylsulfonic acid or toluenesulfonic acid.

The reaction of step b) is frequently performed at temperatures in the range from 80 to 180° C., in particular from 90 to 160° C. Normally, the reaction of step b) will be performed at a pressure in the range from 900 to 1200 hPa. It may be beneficial to remove volatiles, which are formed in the reaction, e.g. water and/or alcohol $R^{4a}$—OH by distillation. In this regard, it may be beneficial to reduce the pressure at the end of the reaction, in order to facilitate destillative removal of the volatiles.

In process 2 of the invention 2,4,6-triamino-1,3,5-triazine, an aldehyde of the formula $R^3$—CHO and the polyether of formula (II) are reacted. Preferred aldehydes are those, mentioned as preferred aldehydes for step a) of process 1. Particular preference given to $C_2$-$C_4$-alkanals, especially to propanal.

The relative amount of aldehyde $R^3$—CHO used in process 2 is frequently in the range from 0.25 to 3.0 mol, in particular from 0.3 to 2.5 mol, especially from 0.35 to 2.3 mol per mol of $NH_2$-groups in the 2,4,6-triamino-1,3,5-triazine or from 0.75 to 9 mol, in particular from 0.9 to 7.5 mol, especially from 1.05 to 6.9 mol per mol of 2,4,6-triamino-1,3,5-triazine.

The amount of polyether of formula (II) used in process 2 will frequently be at least 10 mol-%, in particular at least 15 mol-% and especially at least 20 mol-% or at least 25 mol-% based on the total number of amino groups present in melamine used in process 2. The amount of polyether of formula (II) may be as high as 200 mol-% in particular up to 180 mol-%, based on the total number of amino groups present in melamine used in process 2. Frequently, it is in the range from 30 to 120 mol-%, based on the total number of amino groups present in melamine used in process 2.

Frequently, the amount of polyether of formula (II) used in the reaction of step b) will be at least 30 mol-%, in particular at least 45 mol-%, especially at least 60 mol-% or at least 75 mol-% of melamine used in process 2.

Frequently, the amount of polyether of formula (II) used in the reaction of process 2 will be in the range from 10 to 99% by weight, based on the total weight of melamine, aldehyde $R^3$—CHO and polyether of formula (II). Preferably, the amount of polyether of formula (II) used in the reaction of process 2 will be in the range from 20 to 95% by weight, in particular from 30 to 90% by weight, based on the total weight of melamine, aldehyde $R^3$—CHO and polyether of formula (II).

The reaction of process 2 is preferably performed in the presence of an acidic or a basic catalyst, preferably an acidic catalyst and in particular a Broenstedt acid catalyst. However, Lewis acid catalysts can also be used. The amount of catalyst is frequently in the range from 0.05 to 2% by weight, in particular from 0.1 to 1% by weight, based on the total weight of the reactants, i.e. the melamine, the aldehyde $R^3$—CHO, the polyether of formula (II) and optionally the alcohol $R^8$—OH, if present. Suitable Broenstedt catalysts include but are not limited to organic sulfonic acids, e.g. alkylsulfonic acids such as methyl or ethylsulfonic acid and arylsulfonic acid such as phenylsulfonic acid or toluenesulfonic acid.

Frequently, the reaction of process b) is performed by mixing the aldehyde $R^3$—CHO and melamine in the desired amount, optionally in a solvent, such as water or an alcohol $R^{4a}$—OH, allow the mixture to react at moderate temperatures of at most 80° C., e.g. at the temperatures given for step a) of process 1, preferably in the absence of a catalyst, and than adding the polyether of the formula (II) and optionally a catalyst and heating the reaction mixture to a temperature of at least 80° C., in particular at least 90° C.

The reaction of process 2 is frequently performed at temperatures in the range from 80 to 180° C., in particular from 90 to 160° C. Normally, the reaction of process 2 will be performed at a pressure in the range from 900 to 1200 hPa.

It may be beneficial to remove volatiles, which are formed in the reaction, e.g. water or an excess of aldehyde $R^3$—CHO, by distillation. In this regard, it may be beneficial to reduce the pressure at the end of the reaction, in order to facilitate destillative removal of the volatiles.

A described for step b) of process 1, a part of the polyether of formula (II) may be replaced by an alcohol of the formula $R^8$—OH, where $R^8$ is as defined above. However, the amount of the alcohol of the formula $R^8$—OH will generally not exceed 50 mol-%, in particular 30 mol-%, based on the total amount of alcohol $R^8$—OH and polyether of formula (II). If present, the amount of the alcohol of the formula $R^8$—OH will frequently in the range from 1 to 50 mol-% in particular from 5 to 30 mol-%, based on the total amount of alcohol $R^8$—OH and polyether of formula (II). Preferably, no alcohol of formula $R^8$—OH is present in the reaction of process 2.

Irrespectively of whether process 1 or process 2 is used, preference is given to polyethers of formula (II), wherein $R^5$ has one of the preferred meanings given for A, x and $R^5$, especially to those, wherein A is ethan-1,2-diyl;
x is an integer having a number average value in the range from 5 to 60, especially in the range from 5 to 30;
$R^5$ is $C_1$-$C_4$-alkyl, especially methyl.

Examples of preferred polyethers of formula (II) are $C_1$-$C_{10}$-alkylpolyethylenoxides, $C_1$-$C_{10}$-alkylpolypropylenenoxides, and $C_1$-$C_{10}$-alkylpoly(ethylenoxide-co-propylen-oxide), in particular $C_1$-$C_4$-alkylpolyethylenoxides, and especially methylpolyethylenoxides. Preferred are polyethers of formula (II), which have a number average weight in the range from 140 to 10,000, in particular in the range from 150 to 5,000, more particularly in the range from 200 to 2,000 and especially in the range from 250 to 1,250.

The mono- and polynuclear melamine compounds as described herein, in particular the mixtures, especially the mixtures, which are obtainable by one of the processes 1 or 2, are particularly useful as a dispersant for pigment materials in non-aqueous, liquid pigment compositions.

Therefore, the present invention relates to the use of the mono- and polynuclear melamine compounds as described herein, in particular of their mixtures, especially their mixtures, which are obtainable by one of the processes 1 or 2, in non-aqueous pigment compositions, in particular in an non-aqueous concentrate pigment composition, i.e. in pigment pastes, which can be used for tinting or coloring non-aqueous coating compositions, in particular for coloring solvent-borne paint systems.

The present invention also relates to non-aqueous pigment compositions, comprising at least one mono- or polynuclear melamine compound as described herein, in particular a mixture thereof, especially a mixture, which are obtainable by one of the processes 1 or 2, a pigment material and a non-aqueous liquid diluent.

The term "pigment materials", as used herein, includes both pigments and fillers. In the pigment composition of the invention, the pigment material is in particular selected from the group consisting of pigments and mixtures of at least one pigment and at least one filler. Pigments include organic pigments, inorganic pigments and luster pigments/perlescent flakes.

Examples of suitable organic pigments include azo pigments, disazo pigments, naphthol pigments, benzimidazolone pigments, disazocondensation pigments, metal complex pigments, isoindolinone pigments, isoindoline pigments, the chinophthalon pigments, dioxazine pigments and the polycyclic pigment group consisting of indigo, thioindigo, quinacridones, phthalocyanines, perylenes, perionones, anthraquinones, such as aminoanthraquinones or hydroxyanthraquinones, anthrapyrimidines, indanthrones, flavanthrones, pyranthrones, anthantrones, isoviolanthrones, diketopyrrolopyrrole, and carbazoles, e.g. carbazole violet, and the like. Further examples of organic pigments can be found in the monograph: W. Herbst, K. Hunger *"Industrielle Organische Pigmente"* 2$^{nd}$ Edition, 1995, VCH Verlagsgesellschaft, ISBN: 3-527-28744-2.

Representative examples of organic pigments are:

Monoazo pigments: C.I. Pigment Yellow 1, 3, 62, 65, 73, 74, 97, 183 and 191; C.I. Pigment Orange 5, 38 and 64; C.I. Pigment Red 1, 2, 3, 4, 5, 23, 48:1, 48:2, 48:3, 48:4, 49, 49:1, 51, 51:1, 52:1, 52:2, 53, 53:1, 53:3, 57:1, 58:2, 58:4, 63, 112, 146, 148, 170, 184, 187, 191:1, 210, 245, 247 and 251;

Disazo pigments: C.I. Pigment Yellow 12, 13, 14, 16, 17, 81, 83, 106, 113, 126, 127, 155, 170, 174, 176 and 188; C.I. Pigment Orange 16, 34 and 44;

Disazocondensation pigments: C.I. Pigment Yellow 93, 95 and 128; C.I. Pigment Red 144, 166, 214, 220, 221, 242 and 262; C.I. Pigment Brown 23 and 41;

Anthanthrone pigments: C.I. Pigment Red 168;

Anthrachinone pigments: C.I. Pigment Yellow 147 and 199; C.I. Pigment Red 177;

Anthrapyrimidine pigments: C.I. Pigment Yellow 108;

Benzimidazolone pigments: C.I. Pigment Yellow 120, 151, 154, 180, 181; C.I. Pigment Orange 36 and 72, C.I. Pigment Red 175, 185, 208; C.I. Pigment Brown 25; C.I. Pigment Violet 32;

Chinacridone pigments: C.I. Pigment Orange 48 and 49; C.I. Pigment Red 122, 202, 206 and 209; C.I. Pigment Violet 19;

Chinophthalone pigments: C.I. Pigment Yellow 138;

Diketopyrrolopyrrolpigmente: C.I. Pigment Orange 71, 73 and 81; C.I. Pigment Red 254, 255, 264, 270 and 272;

Dioxazine pigments: C.I. Pigment Violet 23;

Flavanthrone pigments: C.I. Pigment Yellow 24;

Indanthrone pigments: C.I. Pigment Blue 60 and 64;

Isoindoline pigments: C.I. Pigment Yellow 139 and 185; C.I. Pigment Orange 61 and 69, C.I. Pigment Red 260;

Isoindolinone pigments: C.I. Pigment Yellow 109, 110 and 173;

Isoviolanthrone pigments: C.I. Pigment Violet 31;

Metalcomplex pigments: C.I. Pigment Red 257; C.I. Pigment Yellow 117, 129, 150, 153 and 177; C.I. Pigment Green 8;

Perinone pigments: C.I. Pigment Orange 43; C.I. Pigment Red 194;

Perylene pigments: C.I. Pigment Red 123, 149, 178, 179 and 224; C.I. Pigment Violet 29; C.I. Pigment Black 31 and 32;

Phthalocyanin pigments: C.I. Pigment Blue 15, 15:1, 15:2, 15:3, 15:4, 15:6, 16; C.I. Pigment Green 7, 36;

Pyranthrone pigments: C.I. Pigment Orange 51; C.I. Pigment Red 216;

Pyrazolochinazolone pigments: C.I. Pigment Orange 67 and C.I. Pigment Red 216;

Thioindigo pigments: C.I. Pigment Red 88 and 181; C.I. Pigment Violet 38;

Triarylcarbonium pigments: C.I. Pigment Red 81, 81:1 and 169; C.I. Pigment Violet 1, 2, 3 and 27; C.I. Pigment Blue 1, 61 and 62; C.I. Pigment Green 1;

C.I. Pigment Black 1 (Aniline black);

C.I. Pigment Yellow 101 (Aldazine yellow);

C.I. Pigment Brown 22.

Suitable inorganic pigments are e.g.

white pigments, such as titanium dioxide (C.I. Pigment White 6) including crystal forms or modifications thereof, such as rutil or anatas, zinc oxide, zinc sulphide, zinc phosphate, lithopone;

black pigments: iron oxide black (C.I. Pigment Black 11), iron-manganese black, spinel black (C.I. Pigment Black 27); carbon black (C.I. Pigment Black 7); graphite (C.I. Pigment Black 10); chromium-iron-black (P. Brown 29);

inorganic colored pigments: chrome oxide, chrome oxide hydrate green; chrome oxide green (C.I. Pigment Green 48); cobalt green (C.I. Pigment Green 50); ultramarine greene; cobalt blue (C.I. Pigment Blue 28 und 36; C.I. Pigment Blue 72); ultramarine blue; blue manganese; ultramarine violet; cobalt- and manganese violet; red iron oxide (C.I. Pigment Red 101); cadmium sulfoselenides (C.I. Pigment Red 108); cerium sulfide (C.I. Pigment Red 265); molybdenum red (C.I. Pigment Red 104); ultramarine red; brown iron oxide (C.I. Pigment Brown 6 und 7), mixed brown, spinel phases and corundum phases (C.I. Pigment Brown 29, 31, 33, 34, 35, 37, 39 und 40), chromium titanium yellow (CI Pigment Brown 24), chrome orange; cerium sulfide (C.I. Pigment Orange 75); yellow iron oxide (CI Pigment Yellow 42); nickel titanium yellow (C.I. Pigment Yellow 53; C.I. Pigment Yellow 157, 158, 159, 160, 161, 162, 163, 164 und 189); Chromium titanium yellow; Spinel phases (CI Pigment Yellow 119); Cadmium sulfide and cadmium zinc sulfide (CI Pigment Yellow 37 and 35); Chrome yellow (CI Pigment Yellow 34); Bismuth vanadate (CI Pigment Yellow 184).

The luster pigments are single-phase or multi-phase construction lamellar pigments whose color play is characterized by the interplay of interference, reflection and absorption phenomena. Examples are aluminum platelets and one or more times, especially of metal oxides coated aluminum, iron oxide and mica platelets.

Suitable fillers are calcium carbonate, such as natural and precipitated chalksilicon dioxides, such as quartz powder and transparent silicon dioxide, silicates, talc, kaolin, natural and synthetic mica, barium sulphate, metal oxides and hydroxides, such as aluminium oxide and aluminium hydroxide.

The size of the pigment material is preferably in the micrometer range, e.g. the weight average particle diameter may range from 0.1 µm to 500 µm, in particular form 0.2 µm to 100 µm or from 0.5 µm to 50 µm. The weight average particle diameter is usually determined by light scattering methods, e.g. by the method of ISO 13320:2009. The weight average particle diameter may be also determined by sieving analysis.

Generally, the non-aqueous pigment compositions of the invention contain 10 to 70% by weight, in particular 20 to 50% by weight, based on the total weight of the composition, of the pigment component.

In the aqueous pigment composition of the invention the weight ratio of pigment component to mono- or polynuclear melamine compound, calculated in each case as solids, is frequently in the range from 20:1 to 1:5, in particular from 10:1 to 1:2. The concentration of the mono- or polynuclear melamine compound, calculated as solids and based on the total weight of the composition, is generally in the range from 1 to 30% by weight, in particular from 2 to 20% by weight.

The non-aqueous diluent present in the aqueous pigment composition of the invention will depend on the field of application in a known manner. Suitable diluents include organic solvents, such as $C_1$-$C_6$ alkanols, e.g. methanol, ethanol, isopropanol, propanol or n-butanol, ketones, such as di-$C_1$-$C_4$-alkyl ketones, such as acetone, methylethyl ketone, diethylketone, cyclic ketones, such as cyclohexanone, esters of aliphatic acids, in particular of acetic acid, such as ethyl acetate, butyl acetate, methoxyethylacetate, methoxypropyl acetate, aromatic hydrocarbons, such as toluene, xylenes, and aromatic distillates, aromatic ethers, such as anisole, glycol ethers like butyl glycol, or methoxypropylene glycol.

For preparing the pigment composition of the invention, the pigment component is usually dispersed in the non-aqueous diluent in the presence of the at least one mono- or polynuclear melamine compound. The dispersion can be achieved by using conventional techniques, such as high speed mixing, ball milling, sand grinding, attritor grinding or two or three roll milling. The resulting pigment composition may have a pigment to dispersant weight ratio in the above range.

Depending on the intended use, the pigment composition may further comprise one or more conventional additives depending on the intended use. Conventional additives included e.g. rheology additives, non-ionic dispersants, flow auxiliaries, defoamers, pigment synergists, preservatives, and the like.

The pigment composition is frequently formulated as a pigment paste. Such a pigment paste contains the pigment component, the dispersant composition of the invention and an aqueous diluent and optionally additives but generally it will not contain binders.

The pigment compositions of the invention provide for good application properties, such as high color strength, good dispersability in a multitude of liquid compositions. They are particularly useful for tinting solvent borne coating compositions. The resulting paints have high color strength and do not show color change in the rub out-test, as described in DE 2202527.

Suitable coating compositions which can be colored with the pigment compositions of the invention include architectural coatings, industrial coatings, automotive coatings, radiation-curable coatings; paints, including paints for building exteriors and building interiors, for example wood paints, lime washes, distempers and emulsion paints. They can also be sued for coloring solvent borne printing inks, for example offset printing inks, flexographic printing inks, toluene gravure printing inks, textile printing inks, radiation-curable printing inks; waterborne inks, including inkjet inks and color filters.

As explained above, the pigment composition may be included into a coating composition. Such a coating composition contains the pigment component, the at least one mono- or polynuclear melamine compound, a non-aqueous liquid diluent and additionally one or more binders, e.g. film-forming polymers or prepolymers which form a film upon curing. Coating composition may optionally contain conventional additives conventionally used in coating technology, e.g. plasticisers, lubricants, emulsifiers, rheology additives, catalysts, flow auxiliaries, optical brighteners, flame retardants, preservatives, antistatic agents or blowing agents.

Suitable binders are the ones customarily used, for example the ones described in *Ullmann's Encyclopedia of Industrial Chemistry*, 5th Edition, Vol. A18, pp. 368-426, VCH, Weinheim 1991, Germany. In general, the film-forming binder is based on a thermoplastic or thermosetting resin, predominantly on a thermosetting resin. Examples thereof are alkyd, acrylic, polyester, phenolic, melamine, epoxy and polyurethane resins and mixtures thereof. Also resins curable by radiation or air-drying resins can be used. Binders may also be derived from polyvinylalcohol and polyvinylbutyral.

If cold- or hot-curable binders are used, the addition of a curing catalyst may be advantageous. Suitable catalysts that accelerate the curing of binders are described, for example, in *Ullman's*, Vol. A18, loc. cit., p. 469.

Examples of coating compositions containing cold- or hot-curable binders are:

Paints based on cold- or hot-cross linkable alkyd, acrylate, polyester, epoxy or melamine resins or mixtures of such resins, if desired with addition of a curing catalyst;

Two-component polyurethane paints based on hydroxyl-containing acrylate, polyester or polyether resins and aliphatic or aromatic isocyanates, isocyanurates or polyisocyanates;

One-component polyurethane paints based on blocked isocyanates, isocyanurates or polyisocyanates which are deblocked during baking, if desired with addition of a melamine resin;

One-component polyurethane paints based on a tri-salkoxycarbonyl triazine cross linker and a hydroxyl group containing resin, such as acrylate, polyester or polyether resins;

One-component polyurethane paints based on aliphatic or aromatic urethane acrylates or polyurethane acrylates having free amino groups within the urethane structure and melamine resins or polyether resins, if necessary with curing catalyst;

Two-component paints based on (poly)ketimines and aliphatic or aromatic isocyanates, isocyanurates or polyisocyanates;

Two-component paints based on (poly)ketimines and an unsaturated acrylate resin or a polyacetoacetate resin or a methacrylamidoglycolate methyl ester;

Two-component paints based on carboxyl- or amino-containing polyacrylates and polyepoxides;

Two-component paints based on acrylate resins containing anhydride groups and on a polyhydroxy or polyamino component;

Two-component paints based on acrylate-containing anhydrides and polyepoxides;

Two-component paints based on (poly) oxazolines and acrylate resins containing anhydride groups, or unsaturated acrylate resins, or aliphatic or aromatic isocyanates, isocyanurates or polyisocyanates;

Two-component paints based on unsaturated polyacrylates and polymalonates;

Thermoplastic polyacrylate paints based on thermoplastic acrylate resins or externally cross linking acrylate resins in combination with etherified melamine resins; and Paint systems based on siloxane-modified or fluorine-modified acrylate resins.

The invention is hereinafter also described by way of examples.

The following abbreviations will be used
AN: Amine Number [mg KOH/g]
b.w.: by weight
EO: ethyleneoxide
Eq.: equivalents
Mn.: number average molecular weight
SB: Solvent-borne
SC: Solid content
VA: visual appearance Preparation Example: Propanel Based Melamine Resin (Intermediate PM)

In a 600 ml four necked flask, 54.0 g of melamine were suspended in 149.2 g of 1-propanal. The mixture was heated to 40° C. and stirred for one hour. Then, 300 g of methanol were added, and the solution was stirred at 65° C. until it became clear. The excess methanol was removed under vacuum until a viscous mass was left in the reactor. To this ethanol was added at 60° C. and then the obtained mixture was cooled to 5° C. Thereby, a precipitate was filtered off and dried in an oven yielding 109 g of a white powder (~65% yield of theory).

Examples 1 to 3

A 250 ml four necked flask, was charged at 22° C. with intermediate PM of the preparation example, polyether alcohol and 0.5% by weight (based on total amount of both reactants) of para-toluene sulfonic acid. Ingredients and molar ratios based on reactive methylethers of the melamine resin were used according to the table 1 below.

The reaction mass was heated to 110° C., and methanol was removed from the reactor under slight vacuum (ca. 800 mbar). The reaction was completed once no further methanol was collected in the receptor flask (duration ca. 6 hours). The final products were obtained as clear yellowish to orange liquids and used as such. Reactants, reaction conditions and properties of the obtained products are given in the following table 1. The following polyethers were used
A1: methoxypolyethylene glycol with Mn 500
A2: methoxypolyethylene glycol with Mn 350
A3: $C_{10}$-Oxoalcohol with 7 EO

TABLE 1

| Example | PM | Alcohols (weight) | Time [h] | AN [mg KOH/g] | SC [%] | VA |
|---|---|---|---|---|---|---|
| 1 | 25.0 g | A2 47 g | 4 h | 64.6 | 97.2 | Yellow clear liquid |
| 2 | 15.0 g | A1 40.3 g | 5 h | 50.5 | 99.5 | Yellow clear liquid |
| 3 | 11.0 g | A3 27.6 g | 5 h | 52.7 | 99.9 | orange slightly turbid liquid at 22° C. |

Example 4

Into a 2 l four necked flask, melamine (75.7 g) and 1-propanal (232.3 g) were added and stirred at 45° C. for 30 min. Then 840 g of methoxypolyethylene glycol with Mn 350 and 4.8 g of para-toluene sulfonic acid were added and stirred under reflux for another 3 hours. The volatiles were removed by vacuum distillation (500 mbar, max 110° C.). The resulting product (958 g) was obtained as a colorless clear liquid with a solid content of >95%.

Application Test

To reflect the broad applicability of the melamine compounds of the invention on all pigment classes, the dispersants compositions were formulated as pigment pastes with a representative selection of pigments. The following pigments were employed:
Blue pigment: Heliogen® Blue L 6700 F—Cu-phthalocyanine pigment of BASF SE
Red pigment: Bayferrox® Red 130M—micronized iron oxide pigment of Lanxess;
Black pigment: Carbon Black FW 200—a small sized carbon black pigment of Evonik Industries.

For comparative purposes, the following commercial pigment dispersants were used:
Dispersant 1: Efka® PX 4310 (Benchmark): Dispersant based on Acrylate monomers, 70% solution in Methoxypropylacetate
Dispersant 2: Efka® PX 4330: Dispersant based on Acrylate monomers, 70% solution in Methoxypropylacetate
A) Trials With Pigment Pastes With Different Dispersing Agents in SB Alkyd-Melamine System:

The pigment pastes were prepared by mixing the respective amount of pigment, dispersant, and the respective amount of butylglycol to obtain 100 g total weight according to table 2. Additionally 2 mm glass beads were added in a 1:1 weight ratio. After dispersing the paste for 2-4 h in a "DAS 200 Disperser" from LAU, the glass beads were removed by filtration. Pigment loading and weight ratio of dispersant/pigment is given in in table 2:

TABLE 2

|  | Blue 1 [1] | Blue 2 | Red 1 [1] | Red 2 | Black 1 [1] | Black 2 |
|---|---|---|---|---|---|---|
| Butyl glycol | 73 | 63.8 | 29.7 | 22.7 | 80.1 | 75.7 |
| Dispersant [2] | 7.0 |  | 5.3 |  | 4.9 |  |
| Example 4 [3] |  | 16.2 |  | 12.3 |  | 9.3 |
| Blue pigment | 20 | 20 |  |  |  |  |
| Red pigment |  |  | 65 | 65 |  |  |
| Black pigment |  |  |  |  | 15 | 15 |
| Total | 100 | 100 | 100 | 100 | 100 | 100 |

[1] Comparative examples
[2] Conventional dispersant, (70% solution in butanol)
[3] Inventive dispersant (30% solution in butanol)

After equilibration of the pigment pastes for minimum 12 h, their viscosity was determined with an "Anton Paar MCR 302" rheometer at 22° C. and a shear rate of 1 $s^{-1}$ with a cone-plate geometry.

After adding the pigment paste to a solvent borne alkyd-melamine high-gloss finish (parts b.w. of pigment paste per 20 parts b.w. of SB high gloss finish), the finish was applied to a metal substrate by draw down. After drying of the coating the color strength were measured by a "Konica Minolta 2600D" colorimeter. In the following table 3 the values are given relative to a benchmark (dispersant 1) which is defined as 100%.

TABLE 3

|  | 20% Heliogen® Blue L 6700 F | | 65% Bayferrox® Red 130M | | 15% Carbon Black FW 200 | |
|---|---|---|---|---|---|---|
| Dispersing Agent | Viscosity | Color strength | Viscosity | Color strength | Viscosity | Color strength |
| Dispersant 1* | low | 100% | very low | 100% | very high | 100% |
| Dispersant 2* | low | 98% | very low | 77% | very high | 76% |
| Example 4 | low | 101% | low | 96% | low | 90% |

*Comparative

B) Trials with pigment pastes with different Dispersing Agents in SB Resin Containing Acrylic system, based on Joncryl® 507 and 588:

The coating compositions were prepared by mixing the respective amount of pigment, dispersant, resin binder and the respective amount of solvent to obtain 100 g total weight according to table 4. Additionally 2 mm glass beads were added in a 1:1 weight ratio. After dispersing the paste for 4 h in a "DAS 200 Disperser" from LAU, the glass beads were removed by filtration.

Joncryl® 507 and Joncryl® 588 are hydroxyl functional acrylic binders.

TABLE 4

|  | Black 1 [1] | Black 2 |
|---|---|---|
| Joncryl® 507 | 12.5 | 12.5 |
| Joncryl® 588 | 12.8 | 12.8 |
| n-Butanol | 3 | 2.5 |
| Dispersant [2] | 10.5 | |
| Example 4 [3] | | 24.5 |
| n-Butyl acetate | 49.2 | 35.7 |
| Black pigment | 12 | 12 |
| Total | 100 | 100 |

[1] Comparative examples
[2] Conventional dispersant, 70% solution
[3] Inventive dispersant, 30% solution Viscosity and color strength were assessed as described above. The results are summarized in table 5.

TABLE 5

| | 12% Carbon Black FW 200 | |
|---|---|---|
| Dispersing Agent | Viscosity | Color strength |
| Dispersant 1 | low | 100% |
| Dispersant 2 | low | 88% |
| Example 4 | low | 101% |

* Comparative

We claim:

1. A mixture of mono- or polynuclear melamine compounds comprising a 2,4,6 triamino-1,3,5-triazine ring, wherein at least one amino group is of a formula (1):

$$NR^1R^2 \quad (1)$$

where
$R^1$ is H, $CH(R^3)OR^4$, or $R^2$,
$R^2$ is $CH(R^3)O(A-O)_x-R^5$, where
$R^3$ is $C_1-C_{10}$-alkyl, or aryl,
$R^4$ is H, $C_1-C_4$-alkyl, or $C_1-C_4$-alkoxy-$C_1-C_4$-alkyl,
$R^5$ is a hydrocarbon radical having 1 to 40 carbon atoms, which is selected from $C_1-C_{22}$-alkyl, aryl-$C_1-C_4$-alkyl or aryl, where aryl in aryl-$C_1-C_4$-alkyl or aryl is phenyl or naphthyl and is unsubstituted, carries 1 $C_1-C_{10}$-alkyl group, or carries 2 $C_1-C_{10}$-alkyl groups;
x is an integer from 2 to 500, having a number average value in a range of 3 to 200;
A is a $C_2-C_4$-alkan-1,2-diyl radical.

2. The mixture of claim 1, where the mono- or polynuclear melamine compounds are selected from the group consisting of a mononuclear melamine compound of a formula (M1), a binuclear polynuclear melamine compound of a formula (M2), and a polynuclear melamine compound of a formula (M3),

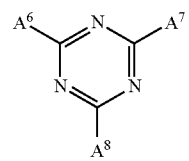
(M1)

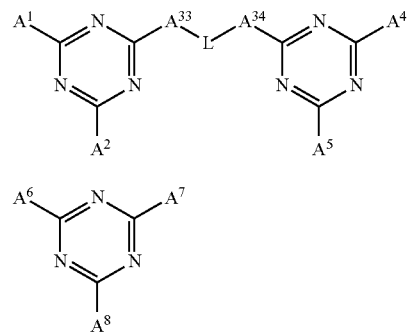

where in formula (M1)
at least one of the radicals $A^1$, $A^2$ and $A^3$ is a radical of the formula (A) as defined in claim 1, while any of the remaining radicals $A^1$, $A^2$ and/or $A^3$ that are not of the formula (A) are of a formula $NHR^x$ or a formula $NWR^y$,
where in formula (M2)
at least one of the radicals $A^1$, $A^2$, $A^4$ and $A^5$ is a radical of the formula (1) as defined in claim 1, while any of the remaining radicals $A^1$, $A^2$, $A^4$ and/or $A^5$ are of a formula $NHR^x$ or a formula $NWR^y$,
L is a bivalent linker $CH(R^3)$ or $CH(R^3)[O-CH(R^3)]_k$, where k is an integer, which is in a range of 1 to 5, and
$A^{33}$ and $A^{34}$ are radicals $NR^z$,
and
where in formula (M3)
at least one of the radicals $A^6$, $A^7$ and $A^8$ is a radical of a formula (Ma)

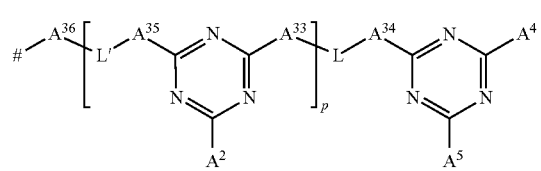
(Ma)

wherein p is 0 or an integer in a range of 1 to 20, provided that in at least one of the groups Ma the variable p is different from 0,
# indicates a point of attachment to the triazine ring of (M3),
L and L' are identical or different bivalent linkers as defined for L in formula (M2),
$A^{33}$, $A^{34}$, $A^{35}$ and $A^{36}$ are radicals $NR^z$,
provided at least one of the radicals $A^2$, $A^4$, $A^5$, $A^6$, $A^7$ and $A^8$ is a radical of the formula (A), while any of the remaining radicals $A^2$, $A^4$ and $A^5$ are of a formula $NHR^x$ or a formula $NR^xR^y$, and any of the remaining radicals $A^6$ and $A^7$ are of formula Ma, formula $NHR^x$, or formula $NR^xR^y$, and where
$R^x$ is $CH(R^3)OR^4$ or $CH(R^3)O-R^8$,
$R^y$ is $CH(R^3)OR^4$ or $CH(R^3)O-R^8$,
$R^z$ is hydrogen, $CH(R^3)OR^4$, or $CH(R^3)O-R^8$, and
$R^8$ is a hydrocarbon radical having from 5 to 40 carbon atoms.

3. The mixture of claim 1, where in formula (1) A is selected from the group consisting of an ethan-1,2-diyl, a propan-1,2-diyl, and mixtures thereof.

4. The mixture of claim 1, wherein formula (1)
A is ethan-1,2-diyl;
x is an integer having a number average value in a range of 5 to 60;
$R^5$ is $C_1$-$C_4$-alkyl.

5. The mixture of claim 1, where in formula (1) $R^1$ is hydrogen.

6. The mixture of claim 1, wherein at least one 2,4,6-triamino-1,3,5-triazine ring bears an amino group of the formula (B):

$$NR^6R^7 \qquad (B)$$

where
$R^6$ is H or $CH(R^3)OR^4$,
$R^7$ is $CH(R^3)O$—$R^8$, where
$R^3$ is $C_1$-$C_{10}$-alkyl, or aryl,
$R^4$ is H, $C_1$-$C_4$-alkyl, or $C_1$-$C_4$-alkoxy-$C_1$-$C_4$-alkyl,
$R^8$ is a hydrocarbon radical having 5 to 40 carbon atoms.

7. The mixture of claim 6, where $R^6$ is hydrogen and $R^8$ is $C_8$-$C_{20}$-alkyl or $C_8$-$C_{20}$-alkenyl.

8. The mixture of claim 1, where the $O(A-O)_x$—$R^5$ present in the melamine compounds amount to 20 to 95% by weight, based on a total weight of the melamine compounds.

9. The mixture of claim 1, where on average at least 10 mol-% of the amino groups of the 2,4,6-triamino-1,3,5-triazine ring are of the formula (1).

10. The mixture of claim 1, wherein at least one feature, i) or ii), is present:
i) $R^3$ is $C_1$-$C_4$-alkyl;
ii) the melamine compounds have a weight average molecular weight in a range of 520 Dalton to 120000 Dalton.

11. The mixture of claim 1, which is obtained by a process 1) or a process 2),
where the process 1) comprises:
a) reacting 2,4,6-triamino-1,3,5-triazine and an aldehyde of a formula $R^3$—CHO and optionally an alcohol $R^{4a}$—OH, wherein $R^3$ is as defined in claim 1 and $R^{4a}$ is $C_1$-$C_4$-alkyl or $C_1$-$C_4$-alkoxy-$C_1$-$C_4$-alkyl;
b) reacting the reaction product of a) with a polyether of a formula (II)

$$R^5\text{—}[O\text{-}A]_x OH \qquad (II)$$

wherein $R^5$, A, and x are as defined in claim 1;
and where process 2) comprises:
reacting a polyether of a formula (II)

$$R^5\text{—}[O\text{-}A]_x OH \qquad (II)$$

wherein $R^5$, A, and x are as defined in claim 1,
with 2,4,6-triamino-1,3,5-triazine and an aldehyde of a formula $R^3$—CHO and optionally an alcohol $R^{4a}$—OH or $R^8$—OH, wherein $R^3$ is as defined in claim 1, $R^8$ is a hydrocarbon radical having 5 to 40 carbon atoms, and $R^{4a}$ is $C_1$-$C_4$-alkyl or $C_1$-$C_4$-alkoxy-$C_1$-$C_4$-alkyl.

12. A process for preparing a mixture of melamine compounds of claim 1, the process comprising:
I)
a) reacting 2,4,6-triamino-1,3,5-triazine and an aldehyde of a formula $R^3$—CHO and optionally an alcohol $R^{4a}$—OH, wherein $R^3$ is as defined in claim 1 and $R^{4a}$ is $C_1$-$C_4$-alkyl or $C_1$-$C_4$-alkoxy-$C_1$-$C_4$-alkyl;
b) reacting the reaction product of a) with a polyether of a formula (II)

$$R^5\text{—}[O\text{-}A]_x OH \qquad (II)$$

wherein $R^5$, A, and x are as defined in claim 1;
or,
II)
reacting a polyether of a formula (II)

$$R^5\text{—}[O\text{-}A]_x OH \qquad (II)$$

wherein $R^5$, A, and x are as defined in claim 1,
with 2,4,6-triamino-1,3,5-triazine and an aldehyde of a formula $R^3$—CHO and optionally an alcohol $R^{4a}$—OH or $R^8$—OH, wherein $R^3$ is as defined in claim 1, $R^8$ is a hydrocarbon radical having 5 to 40 carbon atoms, and $R^{4a}$ is $C_1$-$C_4$-alkyl or $C_1$-$C_4$-alkoxy-$C_1$-$C_4$-alkyl.

13. The process of claim 12, where a reaction with polyether of formula (II) is performed in the presence of a catalytic amount of a Broensted acid.

14. The process of claim 12, where an amount of polyether of formula (II) is in a range of 20 to 95% by weight, based on a total weight of polyether of formula (II), aldehyde of formula $R^3$—CHO, and 2,4,6-triamino-1,3,5-triazine.

15. A method of dispersing a pigment in a non-aqueous, liquid composition, the method comprising: dispersing the pigment in the non-aqueous liquid with a mixture of melamine compounds of claim 1.

16. A non-aqueous pigment composition comprising a mixture of melamine compounds of claim 1, a pigment component selected from the group consisting of pigments and mixtures of at least one pigment and at least one filler, and a non-aqueous diluent.

17. The non-aqueous pigment composition of claim 16, which is a pigment paste.

18. The non-aqueous pigment composition of claim 16, where a weight ratio of pigment component to melamine compound, calculated in each case as solids, is in a range from 20:1 to 1:1.

19. A solvent-borne coating composition comprising the pigment composition of claim 16.

20. The mixture of melamine compounds according to claim 1, wherein $R^3$ is $C_1$-$C_4$-alkyl.

* * * * *